(12) United States Patent
Astle

(10) Patent No.: US 6,274,374 B1
(45) Date of Patent: Aug. 14, 2001

(54) COMBINATION STACKER/INCUBATOR SYSTEM FOR BIOASSAY TRAYS

(76) Inventor: Thomas W. Astle, 607 Harborview Rd., Orange, CT (US) 06477

(*) Notice: Subject to any disclaimer, the term of this patent is extended or adjusted under 35 U.S.C. 154(b) by 0 days.

(21) Appl. No.: 09/398,504

(22) Filed: Sep. 17, 1999

Related U.S. Application Data

(63) Continuation-in-part of application No. 09/198,018, filed on Nov. 23, 1998
(60) Provisional application No. 60/101,104, filed on Sep. 19, 1998.

(51) Int. Cl.[7] .................................................. C12M 1/34
(52) U.S. Cl. ..................... 435/287.3; 435/303.1; 435/307.1; 422/65
(58) Field of Search .................... 435/4, 287.1, 287.3, 435/303.1, 305.1, 307.1; 422/65

(56) References Cited

U.S. PATENT DOCUMENTS

| | | | |
|---|---|---|---|
| 4,720,463 | * 1/1988 | Faber et al. | 435/291 |
| 5,149,654 | * 9/1992 | Gross et al. | 435/287 |
| 5,573,950 | * 11/1996 | Graessle et al. | 435/287.3 |
| 5,744,322 | * 4/1998 | Krejcarek et al. | 435/39 |

* cited by examiner

*Primary Examiner*—David A. Redding
(74) *Attorney, Agent, or Firm*—John H. Crozier

(57) ABSTRACT

In a preferred embodiment, a combination stacker/incubator for microplates, including: a housing; an escapement mechanism disposed at a lower end of the housing to feed the microplates to and from the housing, such that the combination stacker/incubator serves as a stacker for more than one active microplate instrument; and heating apparatus disposed in the housing, such that the combination stacker/incubator serves as an incubator for the microplates.

21 Claims, 3 Drawing Sheets

COMBINATION STACKER/INCUBATOR SYSTEM FOR BIOASSAY TRAYS

CROSS-REFERENCE TO RELATED APPLICATION

The present application claims the benefit of Provisional No. 60/101,104 filed Sep. 19, 1998 and is a continuation-in-part of co-pending U.S., patent application Ser. No. 09/198,018, filed Nov. 23, 1998, and titled ULTRA HIGH THROUGHPUT BIOASSAY SCREENING SYSTEM, the disclosure of which application is incorporated by reference hereinto.

BACKGROUND OF THE INVENTION

1. Field of the Invention

The present invention relates to bioassay incubators generally and, more particularly, but not by way of limitation, to a novel combination stacker/incubator system for bioassay trays.

2. Background Art

In pharmaceutical research, there is an ongoing requirement to screen more compounds for bioactivity against a variety of therapeutic targets. This is accomplished with various bioassay methods. Currently, the standard format in which to conduct bioassays is a microplate measuring approximately 3×5 inches having wells in an 8×12 matrix on 9 mm centers. The trend is to higher density systems using the same 3×5 dimension, but with 384 wells in a 16×24 matrix on 4.5 spacing.

To process the various bioassays, there is a variety of instrumentation available, such as multiple pipettors, 96-and 384-well plate readers, and plate washers. To provide the automation desired, many of these instruments are supplied with plate stackers. The stackers serve as infeed and outfeed devices to the active instrument.

Many bioassays require an incubation period, at elevated temperatures—typically 37 degrees Centigrade. This follows the steps of pipetting reagents into the microplate which starts the reaction. Following this initial incubation period, additional steps of plate washing or reagent addition may be required. These additional reagent additions may be followed by another, or additional, incubation period(s) at elevated temperatures.

Each incubation step requires that the microplates be transported to an incubator device, the transport usually being provided by various shuttle table mechanisms, robotic arms, conveyors, etc. The microplates may pass through an intermediate step of being placed in the stacker before being moved to the incubator. After the incubation period, the microplates are again moved to the stacker from which they are fed to the primary instrument.

Such multiple handling of the microplates represents time that could be employed in additional bioassay procedures.

Accordingly, it is a principal object of the present invention to provide means and method to simplify the handling of microplates and the incubation process.

It is a further object of the present invention to provide such means and method that include heating the stacker such that the stacker serves as an incubator.

It is an additional object of the invention to provide such means and method that are economically achieved and used.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a combination stacker/incubator for microplates, comprising: a housing; an escapement mechanism disposed at a lower end of said first housing to feed said microplates to and from said first housing, such that said combination stacker/incubator serves as a stacker for at least one active microplate instrument; and heating means disposed in said first housing, such that said combination stacker/incubator serves as an incubator for said microplates.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which.

DETAILED DESCRIPTION OF THE PREFERRED EMBODIMENTS

Figure 1:
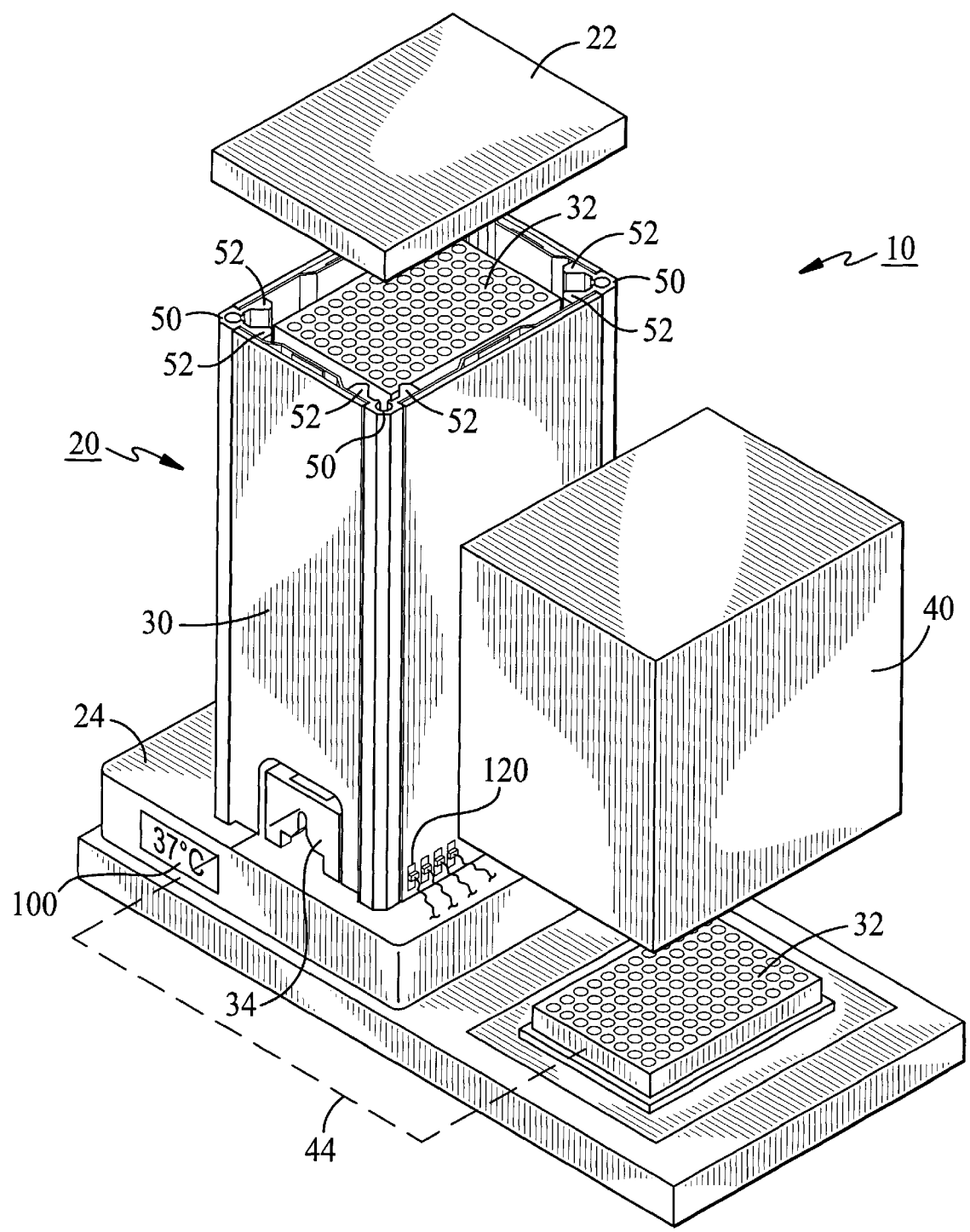
FIG. 1 is a partially schematic and partially exploded isometric view of a bioassay system, including a combination stacker/incubator according to the present invention.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may be seen also on other views.

FIG. 1 illustrates a bioassay system, generally indicated by the reference numeral 10, including a combination stacker/incubator according to the present invention, the latter being generally indicated by the reference numeral 20 and including a removable cover 22. Combination stacker/incubator 20 is mounted on a base member 24.

A stacker is basically a rectangular column or housing 30 that holds a plurality of microplates, as at 32, in an orderly fashion and guides and aligns these plates, in a conventional manner, to a conventional escapement mechanism 34 disposed at the lower end of the housing. Escapement mechanism 34 is operated by an active device 40 that the stacker is serving. Active device may be, for example, a reader or a pipettor that transfers samples and/or reagents to or from microplate 32, aspirates samples from the microplate, and/or washes the wells of the microplate. The exact type of device is not part of the present invention.

Escapement mechanism 34 may be a one-way device—that is, it serves to infeed microplates to active device 40—or it may be a two-way device that both infeeds and outfeeds microplates 32. In the present case, escapement mechanism 34 is a two-way device, since it is required to both put microplates 32 into combination stacker/incubator 20 or take them out of the combination stacker/incubator. There are many different possible arrangements for the stacker portion of combination stacker/incubator 20 and, in particular, for escapement mechanism 34. These arrangements are primarily a function of active device 40 the stacker is to serve and the particular arrangement employed is not part of the present invention.

Represented by broken line 44 on FIG. 1, but not otherwise shown on the drawing figures of the present application, is a transport mechanism to move microplates 32 between active device 40 and combination stacker/incubator 20. This transport mechanism may take the form of shuttle table mechanisms, such as the X-Y shuttle table shown in the above-referenced co-pending patent application, robotic arms, conveyors, etc. The exact mechanism employed is not part of the present invention, as the invention may be used with any of a number of different transport mechanisms.

In use, at least one additional stacker or combination stacker/incubator (not shown) is included to feed microplates 32 one-by-one to active device 40 where a processing step takes place. Microplates 32 are then transported one-by-one to combination stacker/incubator 20 for processing at an elevated temperature and are then transported one-by-one to active device 40 or to another active device. When a further processing step is completed at that active device, microplates 32 are transported one-by-one to the same, or to another, additional stacker or combination stacker/incubator.

Figure 2:
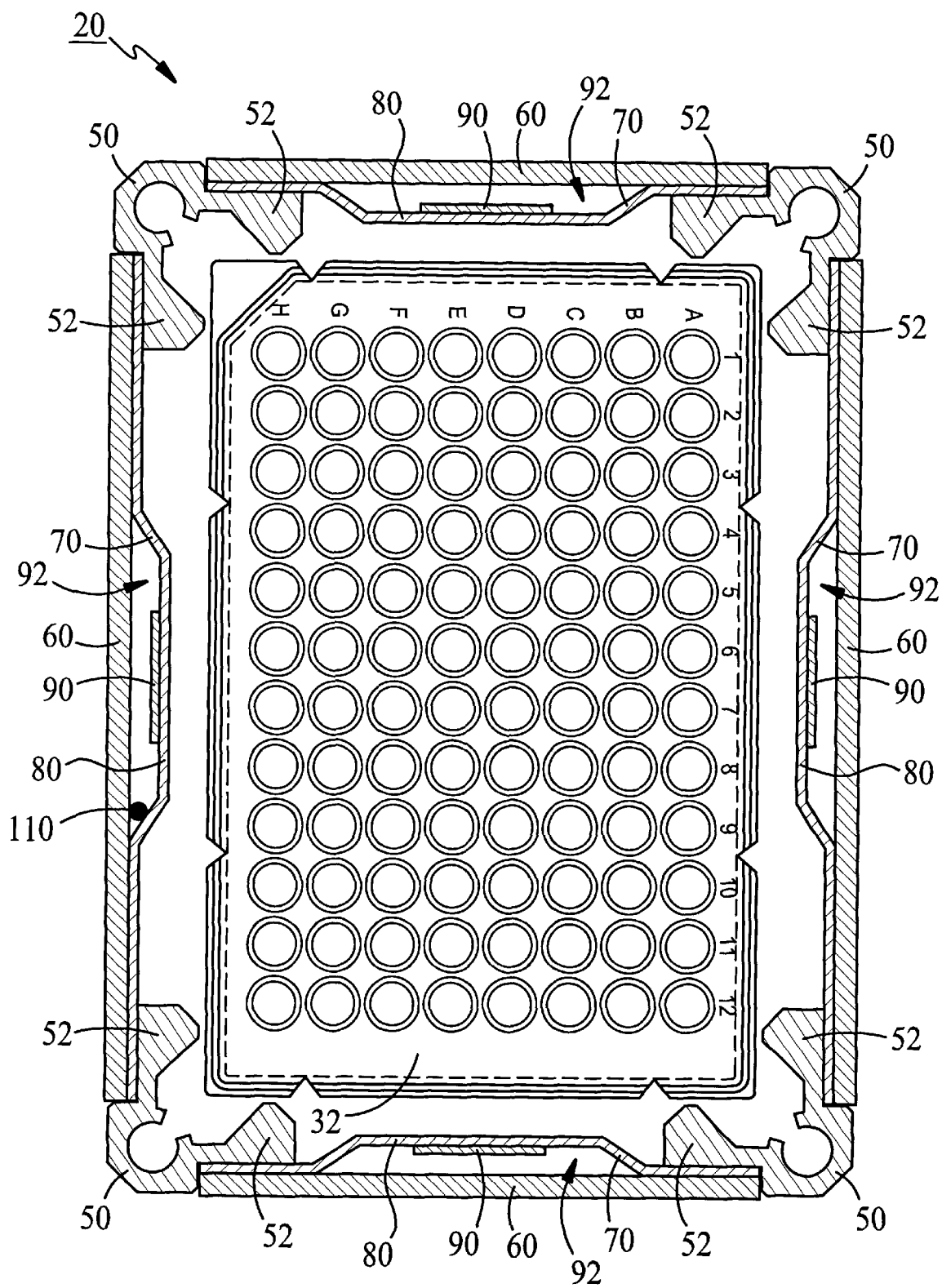
FIG. 2 is a top plan view, in cross-section, of the combination stacker/incubator.

Referring now primarily to FIG. 2, structural support for combination stacker/incubator 20 is provided by four, vertical, extruded, corner angles 50, each having two integral guide portions 52 that position and align stacked microplates 32. The exterior of combination stacker/incubator 20 is closed by four, vertical, smoke-grey, acrylic, outer panels 60 fixedly attached to corner angles 50. Captured between panels 60 and corner angles 50 are four, vertical, aluminum, inner panels 70 captured between outer panels 60 and corner angles 50. Each inner panel 70 has a vertical, inwardly bent, middle section 80 formed therein. Four, vertical, strip heaters 90 are fixedly attached to middle sections 80 in spaces 92 defined between the middle sections and outer panels 60. Spaces 92 provide a form of temperature insulation via dead air space. Strip heaters 90 may be commercially available silicon or rubber strip heaters. A commercially available module 100 (FIG. 1) connected to strip heaters 90 provides proportional, derivative, and integral temperature control, in addition to having a temperature readout.

Strip heaters 90 (FIG. 2) provide temperature uniformity throughout combination stacker/incubator 20, with inner panels 70 serving as heatsinks to uniformly distribute the heat from the strip heaters. A thermocouple 110 attached to one inner panel 70 provides temperature feedback to temperature module. If necessary to provide the desired degree of temperature uniformity in combination stacker/incubator 20, strip heaters 90 may be wound with extra turns of wire at the lower ends thereof to increase the rate of heat transfer in the lower ends.

Combination stacker/incubator 20 is also designed as a removable cassette to enable the user to use the combination stacker/incubator as a transport carrier between compatible devices such as a pipettor and a reader. To make combination stacker/incubator 20 removable from base member 24, four sliding type electrical contacts, as at 120 (FIG. 1), are provided to connect strip heaters 90 and thermocouple 110 (FIG. 2) to module 100. Combination stacker/incubator 20 may thus be simply removed from base member 24 and plugged into a separate, compatible control unit mounted on another device.

Figure 3:
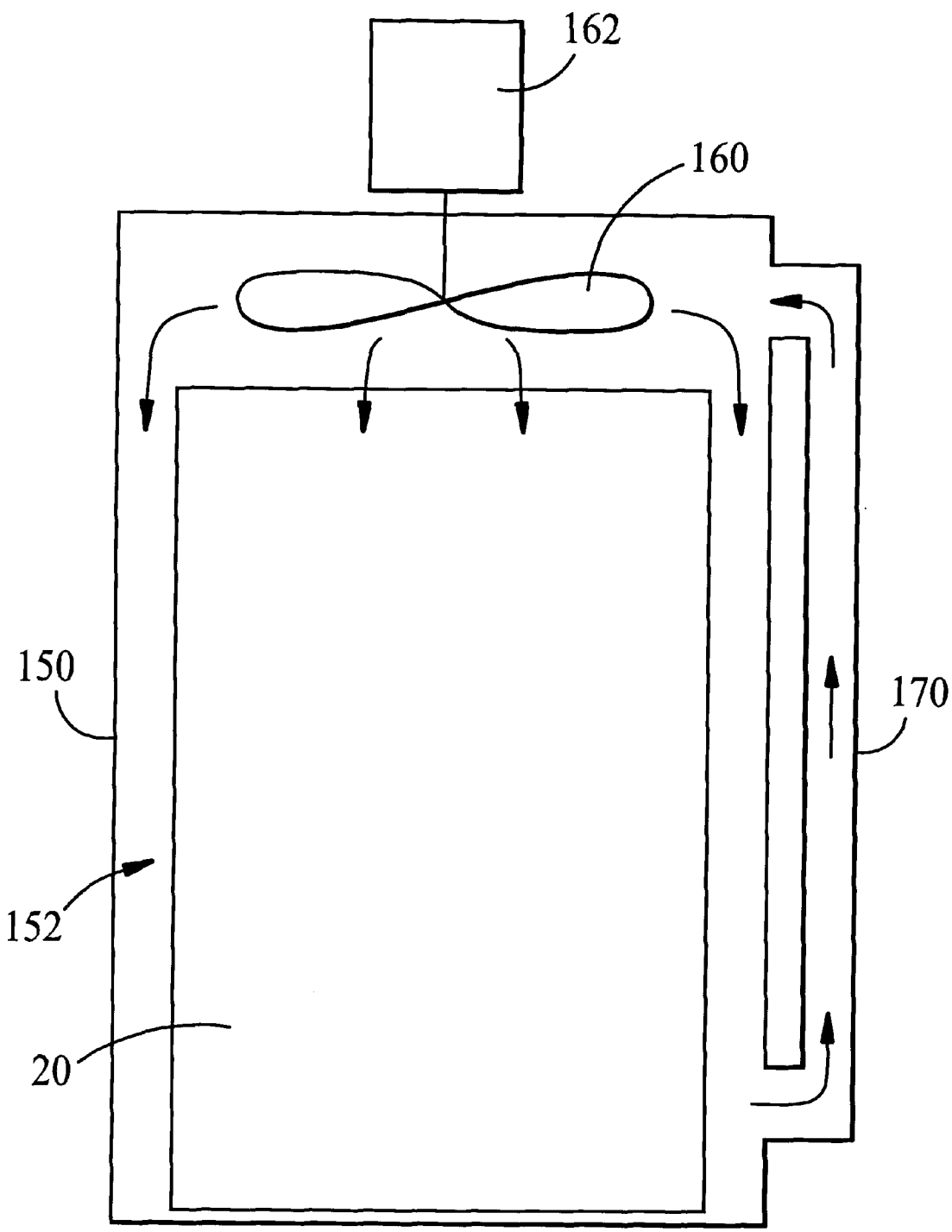
FIG. 3 is a schematic, partially cut-away, side elevational view of the combination stacker/incubator according to a variation of the present invention.

FIG. 3 illustrates a further feature for providing uniform temperature throughout combination stacker/incubator 20. Here, combination stacker/incubator 20 is disposed in a vertical housing 150 such that an air space 152 is defined between the inner surfaces of the walls of the housing and the outer surfaces of the walls of the combination stacker/incubator 20. To assist in maintaining a uniform temperature of combination stacker/incubator 20, a fan 160, powered by motor 162, disposed at the upper end of housing 150 is provided to force air downwardly around the combination stacker/incubator. A return duct 170 connecting the lower and upper ends of housing 150 provides for the recirculation of the air to fan 160. Insulation (not shown) may be provided on the external surface of housing 150, if desired.

The present invention thus extends the value of stackers in bioassay automation. The net result is that an automated pipettor with plate stackers can become a fully integrated bioassay workstation. System throughput is increased. The instrument also increases in value, since it can accomplish a wider range of tasks in the same space.

In the embodiments of the present invention described above, it will be recognized that individual elements and/or features thereof are not necessarily limited to a particular embodiment but, where applicable, are interchangeable and can be used in any selected embodiment even though such may not be specifically shown.

Terms such as "upper", "lower", "inner", "outer", "inwardly", "outwardly", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A combination stacker/incubator for microplates, comprising:
    (a) a first housing;
    (b) an escapement mechanism disposed at a lower end of said first housing to feed said microplates to and from said first housing, such that said combination stacker/incubator serves as a stacker for more than one active microplate instrument; and
    (c) heating means disposed in said first housing, such that said combination stacker/incubator serves as an incubator for said microplates.

2. A combination stacker/incubator for microplates, as defined in claim 1, wherein: said heating means includes inner panels disposed adjacent and extending along walls of said first housing.

3. A combination stacker/incubator for microplates, as defined in claim 2, wherein: said heating means includes heaters attached to said inner panels.

4. A combination stacker/incubator for microplates, as defined in claim 3, wherein: said heaters are attached to said panels in spaces defined between said walls of said first housing and inwardly bent sections of said inner panels.

5. A combination stacker/incubator for microplates, as defined in claim 3, wherein: said heaters are vertically disposed strip heaters.

6. A combination stacker/incubator for microplates, as defined in claim 1, wherein: said first housing is removable from a base on which it is disposed and used as a transport carrier for said microplates.

7. A combination stacker/incubator for microplates, as defined in claim 1, further comprising:
   (a) a temperature controller to control temperature in said first housing; and
   (b) said temperature controller and said primary microplate instrument are under common control.

8. A combination stacker/incubator for microplates, as defined in claim 1, further comprising: a second housing in which said first housing is disposed to provide more uniform temperature of said first housing.

9. A combination stacker/incubator for microplates, as defined in claim 8, further comprising: a fan disposed in said second housing to circulate air around said first housing.

10. A combination stacker/incubator for microplates, as defined in claim 4, wherein: said spaces serve as insulation between said inner panels and said walls.

11. A bioassay system, comprising:
   (a) at least one active microplate instrument;
   (b) a combination stacker/incubator;
   (c) transport means to move microplates between said at least one active microplate instrument and said combination stacker/incubator; and
   wherein: said combination stacker/incubator comprises:
   (d) a first housing;
   (e) an escapement mechanism disposed at a lower end of said first housing to feed said microplates to and from said first housing, such that said combination stacker/incubator serves as a stacker for more than least one active microplate instrument; and
   (f) heating means disposed in said first housing, such that said combination stacker/incubator serves as an incubator for said microplates.

12. A bioassay system, as defined in claim 11, wherein: said heating means includes inner panels disposed adjacent and extending along walls of said first housing.

13. A bioassay system, as defined in claim 12, wherein: said heating means includes heaters attached to said inner panels.

14. A bioassay system, as defined in claim 13, wherein: said heaters are attached to said panels in spaces defined between said walls of said first housing and inwardly bent sections of said inner panels.

15. A bioassay system, as defined in claim 13, wherein: said heaters are vertically disposed strip heaters.

16. A bioassay system, as defined in claim 11, wherein: said first housing is removable from a base on which it is disposed and used as a transport carrier for said microplates.

17. A bioassay system, as defined in claim 11, further comprising:
   (a) a temperature controller to control temperature in said first housing; and
   (b) said temperature controller and said primary microplate instrument are under common control.

18. A bioassay system, as defined in claim 11, further comprising: a second housing in which said first housing is disposed to provide more uniform temperature of said first housing.

19. A bioassay system, as defined in claim 18, further comprising: a fan disposed in said second housing to circulate air around said first housing.

20. A combination stacker/incubator for microplates, as defined in claim 14, wherein: said spaces serve as insulation between said inner panels and said walls.

21. A method of performing at least a portion of a bioassay procedure, comprising the steps of:
   (a) transporting bioassay microplates to an active microplate instrument;
   (b) performing a bioassay operation with said active microplate instrument on each of said microplates;
   (c) transporting said bioassay microplates to a combination stacker/incubator as defined in claim 1 or 11;
   (d) heating said microplates in said combination stacker/incubator; and
   (e) transporting said microplates from said combination stacker/incubator to another step in said at least a portion of a bioassay procedure.

* * * * *